United States Patent [19]
Casu et al.

[11] Patent Number: 5,108,613
[45] Date of Patent: Apr. 28, 1992

[54] PROCESS FOR THE ISOLATION AND PURIFICATION OF MONOSIALOGANGLIOSIDE FROM A STARTING LIPIDIC MIXTURE BY COMPLEXATION WITH ALPHA-CYCLODEXTRIN AND RELATED INTERMEDIATE COMPOUND

[75] Inventors: Benito Casu; Ennio Lanzarotti; Giangiacomo Torri, all of Milan; Annamaria Naggi, Legnano; Armando Cedro, Cislago, all of Italy

[73] Assignee: Crinos Industria Farmacobiologica S.p.A., Como, Italy

[21] Appl. No.: 729,728

[22] Filed: Jul. 15, 1991

[30] Foreign Application Priority Data

Jul. 13, 1990 [IT] Italy ............................ 20942 A/90

[51] Int. Cl.$^5$ .................................................. B01D 61/14
[52] U.S. Cl. ...................................... 210/651; 210/652
[58] Field of Search .............. 536/18.5; 210/634, 637, 210/642, 644, 645, 649-652

[56] References Cited

U.S. PATENT DOCUMENTS 4,868,291  9/1989  Yokoyama et al. ............... 536/18.5

FOREIGN PATENT DOCUMENTS 0319890  6/1989  European Pat. Off. .
0365868  5/1990  European Pat. Off. .
2160423  12/1985  United Kingdom .

OTHER PUBLICATIONS

Carbohydrate Research, vol. 179, 1988, pp. 393-410, Elsevier Science Publishers B.V., Amsterdam et al, "Synthesis and characterization of lyso-GM3 (II3-Neu5Ac lactosyl sphingosine), de-N-acetyl-GM3 (II3-NeuNH2 lactosyl cer), and related compounds".
Biochem. J., vol. 88, 1963, pp. 373-383; D. B. Gammack: "Physicochemical properties of ox-brain gangliosides".

Primary Examiner—Frank Sever
Attorney, Agent, or Firm—Nikaido, Marmelstein Murray & Oram

[57] ABSTRACT

By ultrafiltration of an aqueous solution wherein there have been formerly dissolved alfa-cyclodextrin and a raw lipidic mixture, the latter characterized in that it contains monosialoganglioside (GM1) either as the sole ganglioside or otherwise in a prevailing quantity over the other associated gangliosides, and after the removal of cyclodextrin at the end of the process, it is obtained GM1 with a titer of at least 95%. The present invention concerns also the intermediate complex that it is being formed between the hereabove said monosialoganglioside and alfa-cyclodextrin.

18 Claims, 3 Drawing Sheets

PPM

PROCESS FOR THE ISOLATION AND PURIFICATION OF MONOSIALOGANGLIOSIDE FROM A STARTING LIPIDIC MIXTURE BY COMPLEXATION WITH ALPHA-CYCLODEXTRIN AND RELATED INTERMEDIATE COMPOUND

The present invention concerns a method for obtaining monosialoganglioside, or GM1 according to the nomenclature adopted by L. Svennerholm, J. Neurochem 10 613 1963, from a mixture of lipid formerly extracted from tissues or organs of the nervous system, which lipidic mixture is characterized in that GM1 is lether the sole ganglioside being contained, or otherwise is present in a prevailing quantity over other glycosphingolipids of the family (GD, GT, GQ, etc.).

This condition can be brought about in several known ways, for instance effecting chemical or enzymatic treatments either on the same above said lipidic mixture, or even on the starting organ homogenate where said mixture comes from.

Since many years gangliosides, both as a singular substances and as the corresponding mixtures, have found several and important therapeutic applications and in recent years the interest has been in particular focused on monosialoganglioside.

Turning now to the treatments that have been hereabove mentioned, they can be implemented on the raw extract throughout the following alternative methods:

Enzymolysis with sialidase. It is worth herein noting that the treatment is as well applicable to the starting animal organ homegenate, taking advantage of the fact that the enzyme is present already in the homogenate itself and hence it does not need to be added. Further, in the latter case the raw lipidic extract enriched in GM1 can then be recovered with known methods.

Hydrolysis by means of diluted mineral acids.

Suitable examples of each of the above referred processes are given in the European patent application No. 88120281.6 and in the French patent application No. 258707, respectively.

Turning now to gangliosides, it is herein worth observing that in the corresponding aqueous solutions these compounds are present in micelle aggregates, having a molecular weight of several hundreds of kilodaltons (D. B. Gammack, Biochem. J. 88 373 1963).

Said phenomenon has so far prevented the use of techniques such as ultrafiltration and/or dialysis, for separating gangliosides from the other substances contained in the raw extract formerly obtained by the organs or tissues of the nervous system, since such aggregates could not obviously allow the single molecules to pass through the membrane pores.

Hence the methods that are nowadays employed to isolate gangliosides and in particular GM1 from a raw lipidic mixture take advantage of other techniques, such as fractionation by ion exchange chromatography, using as the eluant a mixture of water with two or more organic solvents.

Said fractionation methods are quite objectionable for several reasons. The main drawback, in the specific case of GM1 isolation, is represented by the time required to achieve the chromatographic separation. Besides, it has been evidenced that the quantity of GM1 actually recovered can vary even very widely from one batch another in comparison to that expected.

As a matter of fact, it has been found a striking dependence on the column efficiency that is affected by two factors, i.e. bed resin regeneration, that must be made after each chromatographic separation, and the next solvent reequilibration.

Other important drawbacks of said methods are the related costs, owing to the fact that, as said, large amounts of mixtures of several organic solvents are required to elute the column.

Further, at the end of the separation, the upper part of the resin bed must be completely removed, and a substitution with an equal volume of fresh resin provided for, since it is irreversibly altered by the impurities of the fractionated lipidic mixture stuck to the resin itself.

Further details of this procedure are being given in example 6, wherein it is described a process for recovering GM1 from the lipidic extract by column ion exchange chromatography, which process lends itself to a direct comparison with process of the present invention.

The main purpose of the invention is thus to provide a process for the isolation and purification of monosialoganglioside from a starting lipidic mixture that contains the substance either as the sole ganglioside, or in a prevailing quantity in comparison with other associated gangliosides of the same family, which process does not comprise any ion exchange chromatographic step and thus remarkably simplifies the procedure that so far has been followed.

Said process is characterized in that monosialoganglioside is obtained by ultrafiltering an aqueous solution containing as solutes the above said raw lipidic mixture, coming from the extraction of tissues or organs of the nervous system, and alpha-cyclodextrin in a determined weight ratio.

Alpha-cyclodextrina, as it is known, are cyclic oligosaccharides constituted of six repeating glucopyranoside units.

According to the invention it has been thus found that by adding to a solution containing the lipidic mixture with the above referred characteristics, a quantity of alpha-cyclodextrin in a determined weight ratio with the former solute, the micelle aggregates are broken and in the conditions adopted for the ultrafiltration a soluble complex is formed with the alpha-cyclodextrin.

As a result of that, the monosialoganglioside can then pass through the membrane pores, wherein the membrane is advantageusly chosen in such a manner that the other lipids could not dyalize in the same conditions.

It is interesting to note here that the process occurs only with alpha-cyclodextrin whereas beta-cyclodextrin, that is a cyclic olygosaccaride constituted of seven glycopyranose units, does not afford any like result as it will be shown in example 10. More in detail, the process for obtaining GM1 according to the invention consists of the following steps:

Ultrafiltration of the solution, wherein the lipidic mixture has been dissolved at a concentration being comprised between 0.5 adn 3.5% w/v, performed through a dialysis membrane with a pore size of 50,000 Daltons or higher, and preferably of 100,000 daltons, and wherein alpha-cyclodextrin is in a ratio by weight at least twice that of the extract.

Concentration of the dialyzate (the permeate) by ultrafiltration through a dialysis membrane with a pore size of 1,000 daltons.

Recovery of the solute which contains the complex of GM1 with alpha-cyclodextrin.

Recovery of GM1 from the above said complex.

It is worth herein noting that the ratio here above referred to of alpha-cyclodextrin to the ganglioside is such as to afford a full complexation of GM1 independently of the titre of GM1 in the lipid mixture.

The ultrafiltration is being carried out by keeping at a constant volume the solution inside the dialysis chamber (i.e. the retenate), by preferably adding a 2% w/v solution of alpha-cyclodextrin.

As a matter of fact it has been found also that plain water, instead of the hereabove said solution, can be used. In this event the quantity of GM1 recovered at the end, although anyway favourably comparable to that given by the column chromatographic methods according to the prior art, is anyway lower than that obtained by using the previous hereabove said ultrafiltration technique.

The final volume of the dialyzed solution (i.e. the permeate) should be at least twice that of the retenate. Preferably, the permeate volume is five times that of the retenate. At the end of the ultrafiltration, the permeate is being advantageously concentrated by ultrafiltration using a membrane with a pore size of 1,000 daltons, until the final solution volume is about one tenth that of the starting permeate.

The concentrated permeate is then preferably liophylized but the solute can be also recovered by precipitation with acetone.

It has been also found that the solute can be precipitated from the corresponding aqueous solution by keeping at +4C. the concentrated permeate, wherein the concentration of GM1 (w/v) should be at least of 0.1% (w/v). Anyway the yield of GM1 by this way is lower than that afforded with the above said procedure.

GM1 can then be recovered by said complex by extraction with methanol or with a corresponding mixture with another organic solvent.

A suitable example of the latter is a solution chloroform/methanol in a ratio 2:1 v/v. The ratio of the volume of the organic solvent, i.e. methanol or the corresponding mixture with another organic solvent, to the weight of the solid, must be at least 5 (v/w) for each extraction.

The extraction step with said solvents shoul be repeated at least three times, more advantageously five times.

It must be pointed out that it is also possible the combination of the two above said decomplexation methods, i.e. extracting the solid coming from the dyalizate at first with methanol, taking to dryness the solution, and extracting then the residue with chloroform:methanol (2:1).

Further, it must herein be still pointed out that with the above described methods for recovering GM1 from the complex with alpha-cyclodextrin, it is left an insoluble residue consisting of the pure complexing agent, that it can be thus collected and employed as such in another operation cycle.

For what concerns the second object of the invention, i.e. the complex between GM1 and alpha-cyclodextrin, FIG. 1 provides evidence of the formation of the product in solution.

The related molar ratios to GM1 are shown in Table I.

Figure 2A:
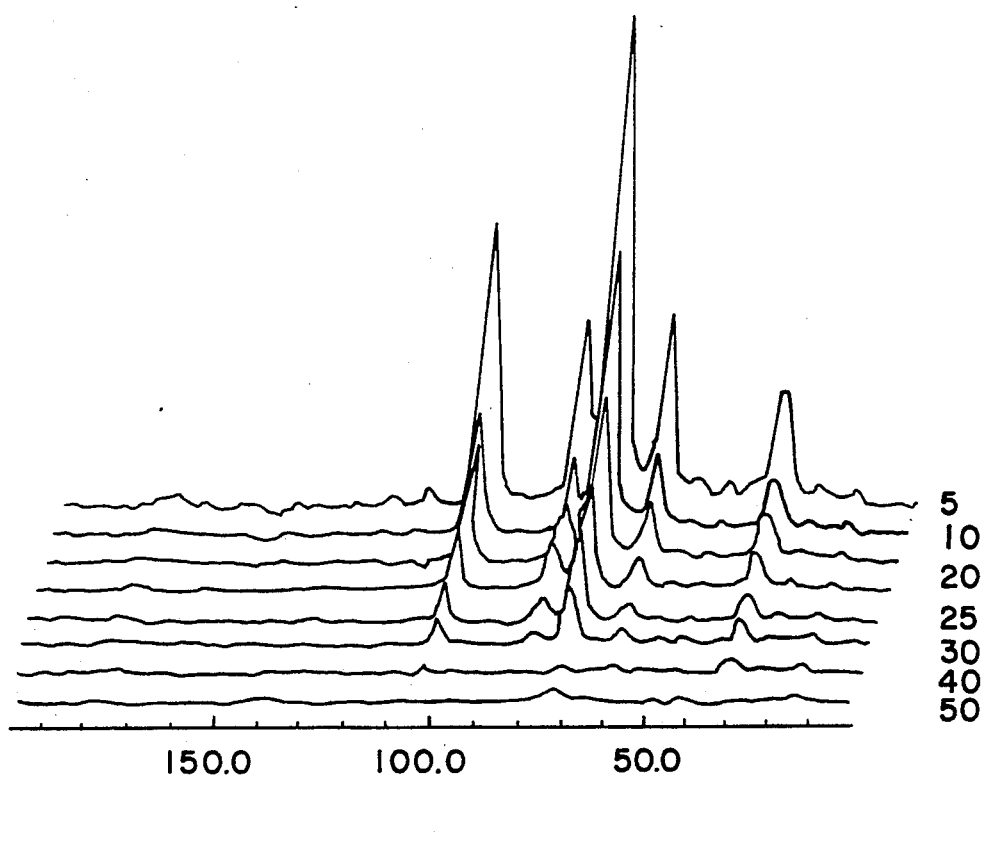
Figure 2B:
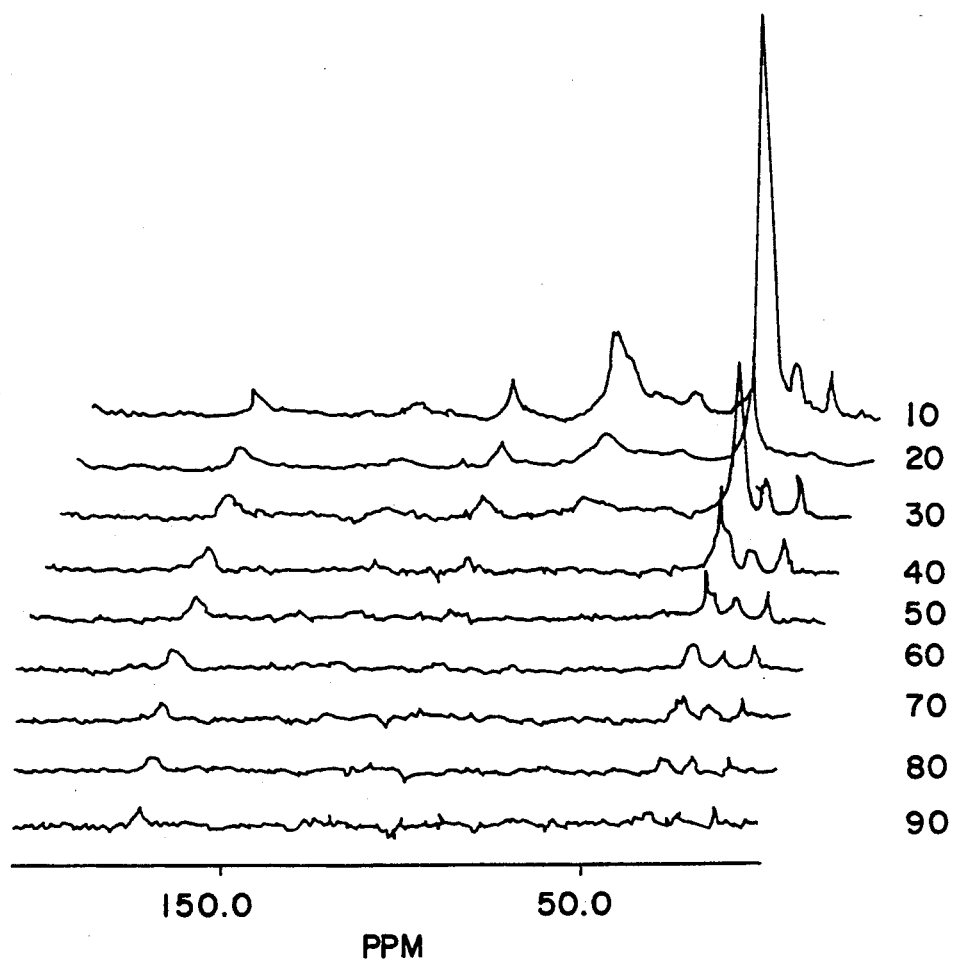

FIGS. 2A and 2B hence show how the spectra (in abscissas ppm), of the complex and of GM1 respectively, vary by giving to the test sample subsequent magnetic impulses at fixed times, taken in microseconds (us) and countened form the start of the experiments.

The interpretation of the spectra, according to the knowledge in this field (see, for instance, the work from T. A. W. Koerner et Alii "High resolution proton NMR studies of gangliosides. 1. Use of homonuclear two dimensional spin-echo J-correlated spectroscopy for determination of residue composition in anomeric configurations" Biochemistry, 1983 22 2676-2687) has been made as follows: signals at 0.82 ppm are attributed to the terminal aliphatic methyl groups of ceramide moiety, that about 1.23 ppm to the methylene protons of ceramide, that at about 1.85 ppm to the acetamido methyl protons (N-acetyl groups of glucosamine and sialic acid), those at 1.9–2.1 ppm to the allylic and alpha-carbonil methylene protons of ceramide.

Of particular interest, for assessing the complex formation, are the signals at 0.82 ppm (terminal methyl groups of the ceramide moiety) and at 1.85 ppm (acetamido methyl protons) since, as it is shown by a space-filling model, the related groups mentioned in brackets protrude outside the molecule and hence these signals are in priciple quite sensitive to changes in the steric environment of the molecule.

Figure 1:
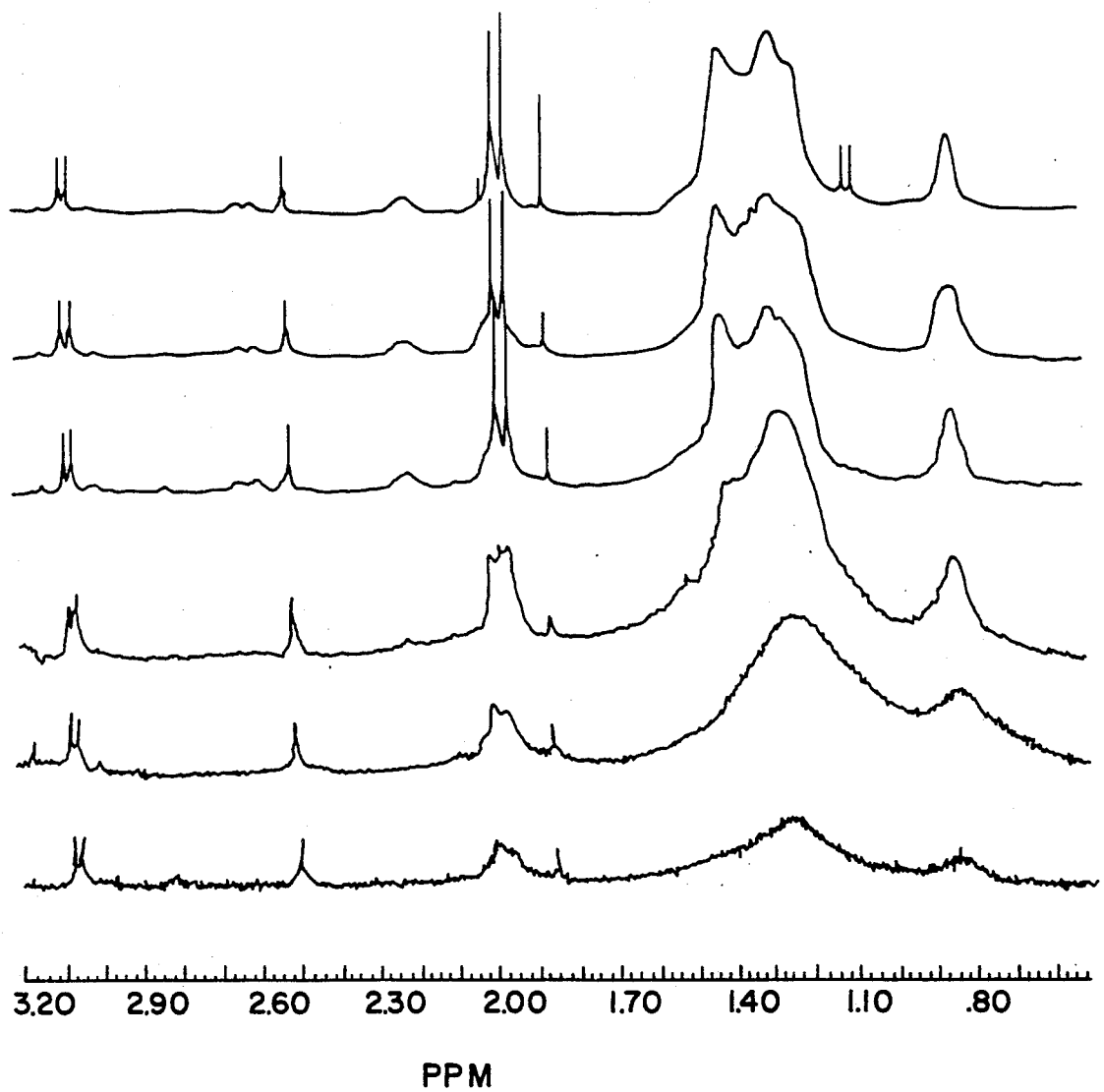
FIG. 1 relates to H-NMR spectra (300 MHz) in $D_2O$ solutions, at a concentration of GM1 of 1 mg/ml. To the solution are then added increasing quantities of alpha-cyclodextrin.

It can thus be seen from FIG. 1 that both the above said signals become more well-resolved and sharp in the presence of increasing quantities of alpha-cyclodextrins, that means that the steric environment is progressively changing in comparison to that formerly existing in the micelle aggregates of GM1.

Further evidence on the complex formation is given by a direct comparison of the related solid state spectra of the substance with that of the starting monosialoganglioside, wherein said spectra were obtained by CP-MAS-$^{13}$CNMR (Cross polarization magic angle spin carbon 13 NMR) spectroscopy and are being featured in the graphs of FIG. 2.

Before explaining the meaning of the spectra it is worth remembering here that the technique is widely used in the structure elucidation of the complexes of cyclodextrins (Y. Inoue et Al., Carbohyd. Res. 159 1 1987).

FIGS. 2A and 2B hence show how the spectra (in abscissas ppm), of the complex and of GM1 respectively, vary by giving to the test sample subsequent magnetic impulses at fixed times, taken in microseconds (us) and countened from the start of the experiments.

TABLE I

| Quantities by weight and related molar ratio of alpha-cyclodestrin to GM1 used in the NMR spectra graphs No. (GM1), 2,4,7,10, of FIG. 1 | | | |
|---|---|---|---|
| NMR graph No. | GM1 (mg) | Alpha-cyclodextrin (mg) | Alpha-cycl./GM1 (molar ratio) |
| (GM1) | 1 | 0 | 0 |
| 1 | 1 | 0,6 | 1 |
| 2 | 1 | 1,2 | 2 |
| 4 | 1 | 2,4 | 4 |
| 7 | 1 | 4,3 | 7 |
| 10 | 1 | 6,2 | 10 |

M.MW of GM1 (sodium salt): 1570,74
M.W. of alpha-cyclodextrin: 972 (J. Szeitli "Cyclodextrin Technology" Kluwer Academic Press Publishers 1988 - in particular page 12)

In this way the relaxation of the magnetic field of the sample is more and more prevented from taking place, so that at the end the signals disapear completely from the spectrum. It can hence be observed that whereas in pure GM1 the time taken to reach this situation is of about 90 us, in the corresponding complex with alpha-cyclodextrin this happens already after 50 us. That means that in the complex the mobility of GM1 (see for instance the related signal at about 30 ppm given by the proton bound to the aliphatic carbon atoms of GM1) is very much prevented in the confront of that of the pure substance. Hence this technique provides a further independent evidence of the complex formation. It must be also mentioned that another demonstration of the formation of this complex is given by the fact that the substance precipitates from the corresponding aqueous solution wherein there have been previously dissolved alpha-cyclodextrin and GM1, latter being at a concentration of at least 0.1%, and provided that the conditions set in the following example 3 are met.

The stoichiometry of the complex has been elucidated by analysing by $^1$HNMR spectroscopy the samples obtained according to the following examples 3 and 7-9.

In particular, there were considered the areas of the signals falling respectively at 5.359 ppm, corresponding to the anomeric proton of the cyclodextrin, and at 1.409 ppm, corresponding to the protons of the terminal methyl groups of the ceramide moiety of GM1.

Each of the related areas was then calculated and their ratio was taken. It was hence found that the molar ratio of alpha-cyclodextrin to GM1 in the complex varied from 4.0 to 6.0.

In the examples herebelow reported all the analytical data are given on a dry weight basis.

EXAMPLE 1

Isolation of monosialoganglioside from a lipidic extract having a titre in GM1 of 57% (w/w).

880 mg of lipidic extract, that had been treated in advance in order to convert all the former gangliosides to GM1 so that at the end the quantity of this substance had been increased up to 500 mg (determined by the related content of sialic according to the method of L. Svennerholm, Biochim. Biophys, Acta 24 604 1957 and then taking as the content of this sugar in GM1 the percentage of 20% according to R. Kuhn et Al., Chem. Ber. 86 866 1963), were dissolved in 80 ml of distilled water.

A solution 10% w/v of alpha-cyclodextrin in water was prepared.

20 ml of the solution, corresponding to a quantity by weight of cyclodextrin twice that of the extract, were added to the former solution, bringing then the final volume to 100 ml. 50 ml were then transferred in an ultrafiltration apparatus equipped with a dialysis membrane having a molecular weight cut-off of 100,000 daltons (disk membrane YM100 AMICON®).

Dialysis was then effected keeping constant the retenate volume by adding a 2% w/v solution of alpha-cyclodextrin.

For each dialysis cycle were collected 50 ml of permeate. The overall related number of cycles was of five.

The solutions of permeate were collected and concentrated up to a final volume of 20 ml by ultrafiltration through a membrane with a molecular weight cut-off of 1000 daltons (disk Membrane YM1 AMICON®). Upon liophylization, were recovered 1050 mg of a solid containing 153 mg of GM1 (determined through the sialic acid assay and taking into consideration the % of sialic acid in the molecule according to the above reference of R. Kuhn et alii).

GM1 was then isolated by extracting the solid of the preceding step with 10 ml of a chloroform/methanol 2:1 (v/v) solution at a time for 5 times.

The organic solution was then taken to dryness under reduced pressure giving 138 mg of GM1 (55% of the theoretical amount), which purity has been assayed, according to the TLC method reported in example 5, to be higher than 95%. The titer of GM1 by sialic acid assay was of 97%.

EXAMPLE 2

Ultrafiltration of a solution containing both the lipidic extract and alpha-cyclodextrin, taking at constant volume the retenate by adding water.

A 50 ml aliquot of the 100 ml solution prepared in example 1 and containing the above referred components, is ultrafiltered as therein described, the retenate being kept at a constant volume by adding water.

After concentration to one tenth (25 ml) of the starting volume, the permeate was precipitated by adding ten volumes of acetone, and gave a solid weighing 1070 mg and containing mg 128 of GM1.

The solid was extracted with methanol, the solvent then taken to dryness under reduced pressure according the procedure reported for the same step in example 1. At the end 113 mg of GM1 (45% of the theoretical amount) were recovered, woth a titer of 96% determined by sialic acid assay, and a purity (TLC of example 5) higher than 95%.

EXAMPLE 3

Precipitation of the complex of GM1 with alpha-cyclodextrin from the concentrated permeate.

The procedure of example 1 was followed, except that the lipid mixture was in a quantity of 1.5 g (GM1 content: 0.645 g, i.e. 43% w/w) dissolved in 15 ml of distilled water, to which have been added 30 ml of the solution 10% w/v of alpha-cyclodextrin.

The metod described in example 1 was then followed for what concerns the procedure up to the obtention of the concentrated permeate solution.

The concentrated permeate solution (20 ml) was left at 4° C. for about 1 day and the precipitate formed collected by centrifugation at 15,000 rpm for 15 minutes and dried at 45 eo at a residual pressure of 0.03 mm Hg for 1 day.

The solid recovered at the end weighed 91 mg and had a content of GM1 of 25.9 mg based on the sialic acid content of the compouns. $^1$HNMR spectroscopy performed as reported already in the disclosure, gave a molar ratio alpha-cyclodextrin/GM1 of 4.0. The solid then underwent decomplexation by extracting it with 2 ml each time of methanol for 5 times and then taking to dryness. The residue was then extracted with 2 ml of chloroform:methanol 2:1 for 5 times. The pooled extracts were taken to dryness and 20 mg of GM1 were recovered titer based on the sialic acid content: 98% purity assay (example 5):higher than 95%.

EXAMPLE 4

Isolation of GM1 from a lipidic mixture with titer in GM1 of 48%.

1.250 g of lipidic mixture with the above content of GM1 were dissolved in 35 ml of distilled water. To the solution 25 ml of alpha-cyclodextrin 10% w/v aqueous solution were then added.

The procedure according to example 1 was then followed. The GM1 that was isolated at the end weight 318 mg (53% of the theoretical amount).

The titer according of the sialic acid assay was 97.5%. Purity by TLC: higher than 95%.

EXAMPLE 5

Assay of purity of the preparations obtained according to the invention.

Purity was assayed by a thin layer chromatographic methos, by direct visual comparison of the intensities of the spots of the impurities of GM1 with those of the related standards.

The sensitivity of the layer chromatographic assay was checked in advance as herebelow reported.

The plates employed were a HPTLC plate (silica gel) and the elution solvent was a mixture of chloroform:methanol:0.3% $CaCl_2$ in water, in the rations 60:35:8.

For each substrance under test thin layer chromatography was performed on two plates at the same time, in order to make it possible the simultaneous evidencing of the spots with each of the herebelow reported reagents.

After development of the plates in a saturated chamber and subsequent drying in an oven, the plates were sprayed respectively with one of the following solutions:
A. Ehrlich Reagent.
B. Anisaldehyde solution. The reagent was obtained by dissolving 1 ml of anisaldehyde in glacial acetic acid, that was then brought to the volume of 100 ml. The solution was then added of 2 ml of 86% w/v sulfuric acid.

After spraying, the plates were then dried in an oven at 100° C. for 10 minutes.

In a first series of experiments, on a plate were layered the following decreasing quantities of the lipidic mixture referred to in example 1 (GM1 titer:57% by weight): 150, 50, 30 and 12,5 mcg.

The plate was sprayed with reagent A. In this way 11 spot were evidenced, the largest corresponding to that of GM1 . 9 sports, having almost the same color intensity, had an Rf value higher than that of GM1.

Said spots, as it was ascertained by direct comparison with suitable standards, corresponded to phospholipids and to other impurities, that were contained in the lipidic extract.

It was as well noted a spot with a very weak color intensity and with an Rf value lower than GM1, identified with the disialoganglioside.

By lowering the quantity of the lipid extract on the plate down to 12,5 mcg, most of the spots formerly evidenced became scarcely distinguishable.

Considering that at a quantity of 30 mcg of the lipidic extract the spots could be detected in TLC, and that the overall quantity of said substrances but GM1 made up to 43% by weight of the starting mixture, i.e. 13 mcg, it was concluded that the detection limit of said compounds by TLC was to be found at about 1 mcg.

In order to evaluate the presence of residual alpha-cyclodextrin in GM1, decreasing quantities of the complexing agent, ranging between 10 to 0.5 mcg, were layered on a second plate. After develpment of the plate, the spots were evidenced with reagent B.

The alpha-cyclodextrin appeared as a dark-red spot at the seeding point. In the conditions adopted, the related spot intensities appeared detectable even down to the lowest quantity layered on the plate, i.e. 0.5 mcg.

The thin layer chromatographic analysis on samples of GM1 obtained according to the examples 1–4 were performed by spotting on a plate, in the order, 200 mcg of the isolated GM1, 30 mcg of the starting lipid mixture and 0.5 mcg of cyclodextrin.

The same procedure was then repeated on a second plate.

In the experiments performed with the preparations obtained with the above reported method, after spraying the plate with reagent A no other spots than that of GM1 were evidenced.

On the plate sprayed with reagent B it was sometimes evidenced at the origin the cyclodextrin spot, which intensity was anyway much lower than that of the standard (0.5 mcg).

EXAMPLE 6

Method for separating GM1 from a raw lipid mixture by ion exchange chromatography (M. Iwamori et Alii, Biochim. Biophys. Acta 528 257 1978).

600 g of Sephadex ® A-25 resin were equilibrated with a buffer solution at pH 7. The buffer was repeatedly changed until the resin gave a neutral reaction to litmus paper. The resin was then collected and subsequantly equilibrated with the eluition solvent, constituted of a mixture of chloroform:methanol:water 30:60:8.

The volume required to accomplish this step was of 9 liters.

The resin was then loaded on a column and eluted with the solvent until the bed height remained constant.

The resin was thereafter loaded with a slurry containing 180 g of raw lipid extract (titer in GM1:50%) dissolved in 5 liters of chloroform:methanol 1:1 and of 500 ml of the resin itself suspended in the elution solvent.

The flow rate was set at 800 ml/hour. Were then collected two fractions, of the volume of 5 and 20 liters respectively. The column was then eluted with chloroform:methanol:0.1M sodium acetate aqueous solution 30:60:8.

The 40 liters of eluate that were collected were then evaporated to a small volume under reduced pressure, taking care of avoiding excessive foaming, ultrafiltered to remove residual salts and then again concentrated to the final volume of 300 ml. GM1 was recovered by adding acetone to the aqueous solution. At the end were recovered 45 g of GM1 I with a titer of 90% (established by sialic acid assay), that corresponded to 50% of the amount of the substance contained in the starting raw lipidic extract.

Before starting a new separation cycle, it was necessary to remove, and substitute with an equal volume of fresh resin, the top of the bed resin that appeared soiled and clogged with the stuck imputies of the lipidic extract.

In this way it was possible to maintain, within certain limits, the starting column separation efficiency and the required flow rate.

EXAMPLE 7

Precipitation of the complex of GM1 and alpha-cyclodextrin from a solution containing the pure components (I). 1.555 g of alpha-cyclodextrin were dissolved in 32 ml of distilled water (solution A). An aliquot of 3.2 ml (0.160 mMoles) was then taken: 24.8 mg of GM1 (0.0158 mMoles) were dissolved in 4 ml of distilled water. The solutions were mixed and left at 4° C. for 19 hours. Recovery of the precipitate was effected as described in example 3.

The solid weighed 10 mg $^1$HNMR spectroscopy gave a molar ratio cyclodextrin/GM1 of 5.1.

EXAMPLE 8

Precipitation of the complex from a solution containing the pure components (II). 49.6 mg of GM1 (0.0316 mMoles) were dossolved in 4 ml of distilled water and added of 3.2 ml of solution A of example 7. After mixing, the procedure of example 7 was followed. The solid recovered at the end weighed 45.2 and had a molar ration alpha-cyclodextrin/GM1 of 4.5 ($^1$HNMR spectroscopy).

EXAMPLE 9

Precipitation of the complex from a solution containing the pure components (III). 12.4 mg of GM1 (0.0079 mMoles) were dissolved in 4 ml of distilled water and then added of 3.2 ml of solution A of example 7. The procedure was then the same.

The solid recovered weighed 10.5 mg had a molar ratio alpha-cyclodextrin/GM1 of 5.7.

EXAMPLE 10

Demonstration that beta-cyclodextrin in the process of the invention does not affor any like or comparable result to that given by alph-cyclodextrin.

440 mg of the same batch of lipidic extract used in example 1 (titer in GM1:57% w/w, corresponding to a quantity of 250 mg) were dissolved in 30 ml of distilled water, added of 1000 g of beta-cyclodextrin and the volume brought then to 60 ml with the same hereabove said solvent.

The solution obtained was perfectly clear and underwent ultrafiltration in the same conditions described in example 1, except that water was added to keep constant the retenate, as reported in example 2.

5 permeate aliquots of 60 ml each were collected. Each permeate fraction and the retenate were then assayed by the TLC method reported in example 5.

It was thus ascertained that the first permeate fraction contained a great quantity of the beta-cyclodextrin, wherein the other subsequent fractions contained only negligible amounts of the substance. The retenate instead did not contain any cyclodextrin.

Very small quantities of GM1 were detected in the first permeate fraction.

Sialic acid assay performed on the retenate, evidenced that the quantity of GM1 therein present was of 235 mg. This amount compared very well with that contained in the starting lipidic extract (250 mg, see above).

We claim:

1. Process for the isolation and purification of monosialoganglioside (GM1) from a lipidic mixture that contains the substance or as the sole ganglioside or either in a prevailing quantity in the confront of other associated gangliosides, which process consists of the following steps:
   (a) ultrafiltration of an aqueous solution wherein there have been previously dissolved both the lipidic mixture and alpha-cyclodextrin through a dialysis membrane with a pore size of 50,000 Daltons or higher.
   (b) concentration of the dialysate (permeate) by ultrafiltration through a dialysis membrane with a pore size of 1,000 Daltons.
   (c) recovery of the solute comprising the complex between GM1 and alpha-cyclodextrin from the concentrated permeate.
   (d) recovery of GM1 from the corresponding complex.

2. Process according to claim 1, characterized in that the concentration of the lipidic mixture in the starting solution is comprised between 0.5 and 3.5%, wherein the quantity of alpha-cyclodextrin is at least twice that of the mixture.

3. Process according to the claim 1, characterized in that membrane pore size of ultrafiltration is preferably of 100,000 daltons.

4. Process according to the claim 1, characterized in that ultrafiltration is carried out by keeping at a constant volume the solution in the dialysis chamber (reteneate).

5. Process according to claim 4, characterized in that the retenate is kept at a constant volume by addition of a 2% w/v of alpha-cyclodextrin in water.

6. Process according to claim 4, characterized in that the retenate is kept at a constant volume by addition of water.

7. Process according to the claim 1, characterized in that the final volume of the dialysed solution (permeate) is at least twice that of the retenate.

8. Process according to claim 7, characterized in that the final volume of the permeate is five times that of the retenate.

9. Process according to claim 1, characterized in that the concentration of the permeate is carried out until the corresponding volume is reduced to about one tenth of that of the starting solution.

10. Process according to claim 1, characterized in that the recovery of the solute comprising the complex between GM1 and alpha-cyclodextrin from the concentrated permeate is made by either lyophilisation, or precipitation with acetone or by keaping the solution at +4C.

11. Process according to claim 10 characterized in that the recovery of the solute is made by precipitation with acetone, ten volumes of the solvent to that of the permeate are being added.

12. Process according to claim 10, characterized in that, the recovery of the solute is made by precipitation at +4C., the concentration of GM1 in the solution w/v being at least 0.1% w/v.

13. Process according to claim 10, characterized in that the solute is recovered from the permeate by lyophilization.

14. Process according to claim 1, characterized in that GM1 is recovered from the corresponding complex with alpha-cyclodextrin by extraction with methanol or with a corresponding mixture of methanol with another organic solvent.

15. Process according to claim 14, characterized in that the ratio volume of the extracting solvent/weight of the solute is of at least 5.

16. Process according to claim 14, characterized in that each extraction step is repeated at least three times.

17. Process according to claim 14, characterized in that the mixture of methanol and another organinc solvent is chloroform:methanol (2:1).

18. Process according to claim 14, characterized in that GM1 is recovered from the corresponding complex with alpha-cyclodextrin by extracting the solid at first with methanol, taking to dryness the solvent, and then extracting the residue with the mixture chloroform:methanol 2:1.

* * * * *